(12) United States Patent
Muthiah et al.

(10) Patent No.: US 9,078,785 B2
(45) Date of Patent: Jul. 14, 2015

(54) ABSORBENT PRODUCT AND METHOD OF MAKING

(75) Inventors: Jeno Muthiah, Bartlett, IL (US); Gerald K. White, Lake Forest, IL (US); Duane R. Rubash, Antioch, IL (US)

(73) Assignee: SYNERGISTIC VENTURES, INC., Homerglen, IL (US)

( * ) Notice: Subject to any disclaimer, the term of this patent is extended or adjusted under 35 U.S.C. 154(b) by 1960 days.

(21) Appl. No.: 11/605,167

(22) Filed: Nov. 28, 2006

(65) Prior Publication Data
US 2008/0125734 A1 May 29, 2008

(51) Int. Cl.
*B05D 1/12* (2006.01)
*A61F 13/15* (2006.01)
*A61F 13/53* (2006.01)
*A61F 13/532* (2006.01)
*A61L 15/60* (2006.01)

(52) U.S. Cl.
CPC ........... *A61F 13/15* (2013.01); *A61F 13/15617* (2013.01); *A61F 13/53* (2013.01); *A61F 13/5323* (2013.01); *A61L 15/60* (2013.01); *A61F 2013/530554* (2013.01)

(58) Field of Classification Search
USPC .......... 428/143, 402.22, 339, 96, 76; 442/181
See application file for complete search history.

(56) References Cited

U.S. PATENT DOCUMENTS

| 5,611,885 | A | 3/1997 | Hansen et al. |
| 5,792,513 | A | 8/1998 | Koslow et al. |
| 6,485,813 | B1 | 11/2002 | Koslow |
| 6,534,572 | B1 | 3/2003 | Ahmed et al. |
| 2003/0175418 | A1 | 9/2003 | Muthiah et al. |
| 2004/0087923 | A1* | 5/2004 | Cole .............................. 604/365 |
| 2004/0142113 | A1* | 7/2004 | Anderson et al. ............. 427/384 |

* cited by examiner

*Primary Examiner* — Ellen S Wood
(74) *Attorney, Agent, or Firm* — Gerald K. White

(57) ABSTRACT

A method of making a pouch-like container product for absorbing liquids comprises joining a first sheet having SAP particles preferably adhered to a first surface with a second sheet to form a container partially filled with such particles. The application of pressure, for example by passing the product through a roll nip, facilitates joining of the sheets and causes the particles to break through at least the one of the sheets to create an opening whereby free volume is created to permit the particles to expand when in contact with a liquid. The resultant product is also described. In an additional product embodiment non-SAP particles may be utilized to break through the sheet(s) and preformed openings may also be included in the sheet(s). Additional SAP material may be placed in between the sheets of the product.

14 Claims, 1 Drawing Sheet

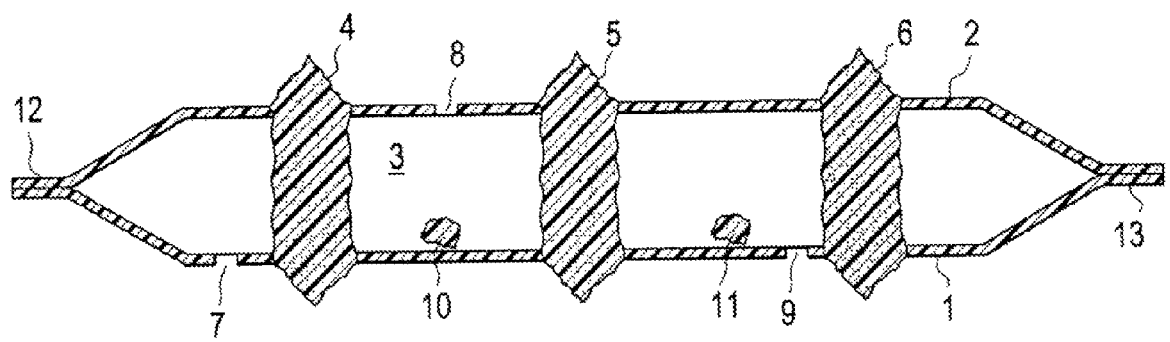

ns and methods for making such products. The invention may be
ABSORBENT PRODUCT AND METHOD OF MAKING The present invention relates to liquid absorbent products and methods for making such products. The invention may be used as a core element for absorbent products, such as diapers, training pants, feminine care products, and the like or as a water collection, storage, and dispensing element for applications such as irrigation, erosion control, or plant watering and plant root growth control.

BACKGROUND OF THE INVENTION

Disposable absorbent products currently find widespread use in many applications. For example, in the infant and childcare areas, diapers and training pants have generally replaced reusable cloth absorbent articles. Other typical disposable absorbent products include feminine care products such as sanitary napkins, panty shields, or tampons; adult incontinence products; and health care products such as surgical drapes or wound dressings. A typical disposable absorbent product generally comprises a composite structure including a top sheet, a back sheet, and an absorbent core structure between the top sheet and back sheet. These products usually include some type of fastening system for fitting the product onto the wearer.

The use of water-swellable, generally water-insoluble absorbent materials, commonly known as superabsorbent polymers ("SAP"), in disposable absorbent personal care products is known. Such absorbent materials are generally employed in absorbent products in order to increase the absorbent capacity of such products while reducing their overall bulk. Such absorbent materials are generally present in absorbent products in the form of small particles and may be included in a fibrous matrix, such as a matrix of wood pulp fluff. A matrix of wood pulp fluff generally has an absorbent capacity of about 6 grams of liquid per gram of fluff. The superabsorbent materials generally have an absorbent capacity of at least about 10, preferably of about 20, and often of up to 100 times, and even up to 300 times, their weight in water. Clearly, incorporation of such superabsorbent materials in disposable absorbent products can reduce the overall bulk while increasing the absorbent rate and capacity of such products.

The absorbent products mentioned above, such as baby diapers, adult incontinence devices, and feminine hygiene products, may be made with a cellulose fiber fluff-based absorbent core sandwiched between a liquid pervious top sheet, which allows the unobstructed passage of fluid to the absorbent core, and a liquid impervious backing sheet usually of plastic material, which contains the absorbed fluid and prevents it from passing through the absorbent core and soiling the undergarments or clothing of the wearer of the absorbent article. The core product of the present invention does not require, but may contain, fibrous material. In various embodiments of the present invention, SAP powder is held within a container, with or without fibrous material. The container may optionally include openings on either of its surfaces that are pre-formed and/or formed during manufacture so as to admit liquids to become absorbed by the SAP powder or even to become collected in liquid form. As will be disclosed in more detail later, the openings created during manufacture of the absorbent product by the SAP particles during the pressing step are sufficient for most applications.

In recent years, market demand for thinner and more comfortable absorbent articles has increased. Ultra-thin feminine napkins are no longer constructed from loose wood pulp, which tends to give a bulky product, but with a roll wood-based air-laid absorbent cores in which a roll or coil of pre-formed absorbent core material is unwound directly onto the absorbent pad-making machine without the defiberization step required for fluff-based products. The roll wood-based approach results in a product thinness, which cannot be achieved by loose fluff-based technology. As will be seen later, the present invention can produce thinner absorbent products that have comparable or improved absorbency properties to thicker products. The present invention thus serves to further reduce product thickness and weight.

Although a given SAP particle has the capability to absorb and contain a liquid, in actual practice it is difficult to efficiently utilize this capability. If the SAP particles are located as a mass in close proximity to each other, the rate of absorption and the capacity to retain absorbed liquid are reduced because the liquid will not be able to reach, or only slowly reach, the interior of the SAP mass. As the outer surface area of the SAP mass begins to absorb liquid, in effect, a barrier is created that substantially slows the rate of liquid absorption. Consequently, it is understood that the separation, as well as the size, of the SAP particles are important considerations. Attempts to address this problem have included adhering the SAP particles to non-SAP material by hot melt adhesion or the use of resinous binders, including both thermoplastic and thermosetting types. There are problems associated with these attempts. The use of such adhering materials causes encapsulation or partial encapsulation of the SAP particles and thereby prevents or reduces the surface area available for efficient liquid absorption. In addition, free volume for particle expansion is compromised. Furthermore, even when the SAP particles are initially adhered, as the particles expand and soften during the absorption phase, the particles tend to separate and migrate toward other SAP particles thereby further reducing liquid absorption and free volume. The above prior art problems are beneficially addressed by the free volume considerations underlying the present invention.

In any event, many products for absorbing liquids and processes for making thereof are described in the art. Typical of such products and processes are those described in Assignee's co-pending U.S. patent application Ser. No. 10/357,907, filed Feb. 4, 2003, and published on Sep. 18, 2003, under Publication No. US-2003-0175418-A1; U.S. Pat. No. 5,792,513; U.S. Pat. No. 6,485,813; U.S. Pat. No. 5,611,885; and U.S. Pat. No. 6,534,572. However, none of these patents or patent publications is believed to possess or teach the unique combination of advantages of the present invention.

In general, the absorbent product of the present invention may utilize SAP particles having a predominant amount of particles on the order of a maximum average particle size of about 500 microns and a minimum average particle size of about 100 microns and thereby more rapidly absorb liquids, such as water, body fluids, urine, blood, etc., than possible when using coarser particles of the same weight. However, it should be understood that lower sized particles may be mixed with larger sized particles to further increase the rate of liquid absorption. Such increased rapidity of absorption is due to the larger total surface area of the fine particles. Rapid absorption is particularly important when the absorbent product is a portion, such as a core, of a diaper product or the like. The present invention also involves spacing absorbent SAP particles apart from each other and provides the necessary free volume surrounding the particles to permit the particles to expand more readily during absorption of a liquid to improve absorption capacity, rate, and efficiency and thereby permitting the use of less SAP particles than if such SAP particles were not extended through the sheet surface(s) and not so spaced apart and did thus not have as much free volume into which to expand. Creating and maintaining free volume also has the advantage of providing a space to collect and store liquids, such as water, for subsequent dispensing to, for example, plant root systems. Other processes involving adhering SAP particles to substrates have the distinct disadvantage of covering, or even encapsulating, a surface portion of the SAP particles, thereby reducing the effectiveness of the SAP particles.

While the present invention is primarily described in connection with diaper products, it will be understood by those skilled in the art that the product of the invention may be used in water collection, storage, and dispensing applications including irrigation, erosion control, and for plant watering and plant root growth control.

SUMMARY OF THE INVENTION

The present invention pertains to a method of making an absorbent product and the resultant product of such method. The method generally comprises providing a first sheet, preferably having an adhesive coated on a first side surface, and a second side surface that is opposed to the first side surface. Particles of SAP are then applied to the first surface. The SAP particles are substantially spaced apart from each other so as to create free volume for sideways expansion. A surface of a second sheet is then placed against the coated surface of the first sheet to join the sheets and to form a product that is partially filled with the particles. Pressure is applied to the thus arrayed first and second sheets to cause the particles to break through the surface of one or both of the sheets thereby forming an opening and creating free volume for the particles to expand into when in contact with a liquid.

One product of the invention generally comprises a first sheet having a first side preferably coated with an adhesive and having particles of SAP adhered to the first surface. A second sheet is joined to the surface of the first sheet to form a container being partially filled with the particles. The particles are substantially spaced apart from each other and extend through openings created in one or both of the sheet surfaces thereby creating free volume for the particles to expand into when in contact with a liquid. The particles may also extend through the other sheet to further enhance absorbency of the liquid.

A second product of the invention generally comprises a first sheet having a first side preferably coated with an adhesive and having non-SAP particles adhered to the first surface. A second sheet is joined to the surface of the first sheet to form a container being partially filled with SAP material such as particles or a film, chips, or films. The non-SAP particles are substantially spaced apart from each other and extend through openings created in one or both of the sheet surfaces thereby creating free volume to permit the SAP material to expand when in contact with a liquid. This product is especially adapted for long term use applications such as in irrigation, erosion control, plant root ball watering, and plant root direction control.

A third product of the invention comprises first and second sheets joined together to form a container being partially filled with SAP material such as particles, chips, or films. One or both sheets have openings to permit the entry and exit of a liquid, such as water. This product is especially adapted for applications such as those described in the preceding paragraph.

BRIEF DESCRIPTION OF THE DRAWINGS

The sole FIGURE is an illustration of a vertical cross section taken along a longitudinal axis of the product of the invention.

DETAILED DESCRIPTION OF THE INVENTION

The products of the present invention are suited for use as cores in disposable products including disposable absorbent products such as diapers, diaper liners, training pants, wraps and covers, adult incontinence products, and bed pads; incontinence devices; feminine hygiene products such as sanitary napkins, panty shields, or tampons; other absorbent products such as wipes, bibs, wound dressings and surgical capes or drapes, mattress covers and puddle pads. Accordingly, in another aspect, the present invention relates to a disposable absorbent product utilizing the absorbent core of the present invention as a component. For example, such product could be used alone or in combination with other absorbent materials in previously-described absorbent products such as diapers, feminine hygiene products, adult incontinence products, wiping sheets, surgical drapes, etc. An important aspect of using this product for absorbent product applications is that the size and weight of the absorbent product would be reduced, thereby conferring benefits of comfort and appearance to the user and also creating less solid waste per unit. This latter advantage is an important factor for waste disposal sites. Some absorbent products contain an acquisition layer to absorb and then more slowly disperse urine or other liquid into a superabsorbent polymeric powder-containing portion of the absorbent product. In accordance with this invention, the use of fine superabsorbent polymeric powder with its attendant rapid absorption rates may reduce the size of, or eliminate the need for, such acquisition layer.

The products of the present invention are also suited to be used as secured elements or containers having sufficient free volume to enhance the collection, storing, and dispensing of water for irrigation applications. Simply placing SAP particles in the ground does not address or provide the requisite free volume and thus the potential absorption properties of such SAP particles are not efficiently realized. The elements are placed underground and preferably secured at a desired location(s). Placement may be accomplished by digging a hole in the ground, placing and securing the element in such hole, and covering the element. Alternatively, the element may be placed into the ground, for example, by insertion by pushing hollow tube-like members or composite strips that contain the element into the ground. The element may be adhered to the interior of the tubular member or contained in the member as a strip, wrapped spiral, oval, cylinder, triangle, or the like. The tubular member preferably may have sidewall openings to permit water ingress and egress. The tubular member may comprise a rigid material such as metal, plastic, wood, etc. However, a pouch-like fabric container made from, for example, burlap is also suitable for some applications. The tubular member may be of any desired shape and may include, for example, a half circle or angular member. Such arrangement serves to locate and secure the element at a desired underground location. Once placed and secured underground, the element functions to collect, store, and ultimately dispense water for soil irrigation. Those skilled in the art will understand that such system may collect and store rainwater and/or artificially applied water and then dispense such water at a later time for watering purposes as the watered soil dries. Securing the placed element at a desired underground location may be accomplished by affixing or securing the element to a stable element so that the placed element remains at the desired location and does not move to a less desired and less effective location.

When the product of the present invention are used as elements to control or minimize soil erosion, the element may be placed underground with use of any of the above-described irrigation elements and/or placement techniques. Especially when relatively fine SAP particles are used in the erosion control element, water that would otherwise cause soil erosion is rapidly collected, stored, and later dispensed when the soil becomes drier. It is important to appropriately locate and secure the erosion control element because erosion is a repetitive event. The erosion control element may be secured in the manner mentioned above in connection with the irrigation element or may be secured to a stable underground element such as a rod, screen, stake, pole, hollow cylinder, cage, etc. or any other stable element.

The products of the present invention may also be used for horticultural applications involving water collection, storage, and dispensing for trees or other plants contained within wrapped or unwrapped balls located in or above the ground. Such products may also be used in connection with plant root direction control processes. The elements and placement techniques described in connection with irrigation and erosion control elements are applicable for these applications as well.

The method of the present invention is used to make a product for absorbing liquids that is useful for, but not limited to, applications such as those described above. In such method, SAP particles are applied to and coat an adhesive coated side of a first sheet. Optionally, non-woven fabrics or woven fabrics having openings or other materials that may be absorbent or non-absorbent may be placed on the SAP particle coated surface of the first sheet prior to placement of the second sheet. Such materials may serve to further increase free volume for the SAP particles to expand into when coming in contact with a liquid. It is also contemplated that these materials may be placed on the adhesive coated surface prior to application of the SAP particles. In any event, the thus coated first sheet is then placed against or contacted with a second sheet to join the sheets and then pressure is applied to the joined sheets to further enhance joining (when the steps of placing and pressing are performed separately) and to cause the SAP particles to break through at least the surface of one of the sheets thereby creating free volume for the SAP particles to expand when in contact with a liquid. The steps of joining the sheets and breaking through the surface of at least one of the sheets with the SAP particles may be performed separately or concurrently.

Superabsorbent polymeric powders suitable for use in the present invention include, but are not limited to, a wide variety of anionic, cationic, and nonionic materials. Suitable polymers include polyacrylamides, polyvinyl alcohols, ethylene maleic anhydride copolymer, polyvinylethers, polyacrylic acids, polyvinylpyrrolidones, polyvinylmorpholines, polyamines, polyethyleneimines, polyquaternary ammoniums, natural based polysaccharide polymers such as carboxymethyl celluloses, carboxymethyl starches, hydroxypropyl celluloses, algins, alginates, carrageenans, acrylic grafted starches, acrylic grafted celluloses, chitin, chitosan, and synthetic polypeptides such as polyaspartic acid, polyglutamic acid, polyasparagins, polyglutamines, polylysines, and polyarginines, as well as the salts, copolymers, and mixtures of any of the foregoing polymers. Anionic polyacrylamide polymers are an example of a suitable material. These particles have sharp edges thereby facilitating the ability of the particles to break trough the surface of the sheet(s) during the pressing step of the present invention.

SAP particles, powders, films, or chips of starch-containing compositions are also suitable for use in the present invention despite the fact that such compositions are not generally strong enough to break through the top and bottom sheets of the product. When pressure is applied perpendicularly to the sheets, starch-containing SAP particles typically become crushed into a finer powder rather than breaking through at least one of the sheets. Despite such lack of strength, starch-containing SAP products may be used in combination with stronger particulate SAP products such as polyacrylates and polyacrylamides and non-SAP particles such as sand, rocks, metals, wood, and the like. Suitable starch-containing SAP products are sold under the trade name "Zeba" by ATI, Beaverton, Oreg. U.S. Pat. Nos. 3,425,791; 3,661,815; 3,981,100; 3,997,484; 4,134,853; and 4,194,998 are illustrative, but not limiting, of such starch-containing compositions. Many of such products are naturally occurring. The second and third of the patents listed above report water absorption up to 1000 times the weight of the composition. Such absorption capacity exceeds that of other typical SAP compositions such as polyacrylate and polyacrylamide compositions.

In the context of this invention, SAP particles having an average size from about 100 about 500 microns are typically used. The particle size is selected to be sufficiently large to penetrate and break the surface of one or both sheets when pressure is applied to the sheets and to maintain a sufficient distance or separation between the respective inner surfaces of the container pouch and thereby create and maintain sufficient free volume within the container to permit the needed expansion of SAP particles upon contact with a liquid.

With the above-enumerated SAP particle size considerations in mind, it is possible to further enhance the performance of the present invention by utilizing a mixture of fine and coarse SAP powders within the container. As mentioned above, the relatively coarse SAP particles having a size ranging from about 100 to 500 microns serve to maintain sufficient distance or separation between the respective inner surfaces of the container pouch to maintain sufficient free volume within the container to permit the needed expansion of the SAP upon contact with liquid. On the other hand, the additional presence of relatively fine SAP particles on the order of from about 20 to about 100 microns serves to enhance the speed of liquid absorption. Thus the mixture of coarse and fine SAP particles permits rapid liquid absorption but yet further creates and maintains the necessary free volume in the product to permit SAP powder expansion.

At least one sheet may be a plastic, such as polyvinyl chloride (PVC), or a copolymers of PVC and vinyl acetate or ethylene vinyl acetate provided that the sheets are sufficiently brittle to permit penetration and breaking by the SAP particles during the pressing step. In general, plastics containing plasticizers in amounts that impede breakage are not used for both sheets in the invention. Water-soluble plastic sheets are not typically used as the integrity of the container could be compromised. However, for short term applications or where container integrity is not necessary, water-soluble plastics could be used. Cellulosic sheets, such as paper, and metallic foils are also contemplated for some applications. The sheet or sheets intended to be broken typically have a thickness ranging from about 0.05 mils to about 0.5 mils. Provided that at least one of the sheets meets the requirements of the invention, the other sheet may be selected from materials that do not meet such requirements.

One or both of the sheets may be coated with an adhesive either prior to or applied, such as by spraying, during the process. Typically the first or lower sheet is coated with an adhesive although the SAP particles could be placed on a sheet having no adhesive and the a second sheet having an adhesive could be placed over and pressed against the first sheet to adhere the sheets and thereby form the container.

For example, U.S. Pat. Nos. 5,662,758; 5,871,607; and 6,194,062 disclose sheets or films having pressure sensitive coatings protected from inadvertent adherence. Sheets of this type, although certainly not essential to the practice of the present invention, would be advantageous to the practice of the invention from a sheet handling aspect if coils of sheet were to be used as a starting material. In any event, the sheets disclosed in the above-mentioned patents are suitable for use in the present invention for one or both of the sheets. Such suitability is because these sheets are sufficiently tacky to initially adhere the SAP particles to the first sheet and be sufficiently weak to permit the so-adhered particles to break through the surface of the sheet during the pressing step. It is contemplated that solid polymeric adhesives such as acrylic (poly isooctyl acrylate), styrenic (styrene copolymers), and elastomeric (urethane type) may be used in the present invention. Typical of these types of solid adhesives are Loctite's Contact Adhesive 30537 and Adchem's adhesive transfer tape Type 1666 (2 mils).

To maximize both the rapidness of liquid absorption and overall absorption properties of the product of the invention, it is necessary to provide for sufficient free volume surrounding the adhered SAP particles to permit expansion of such particles when making contact with a liquid. By spacing-apart individual particles during application to the adhesive coated surface of one of the sheets, free volume is created along the sides of the particles and sideways expansion facilitated. Should the particles be placed together or very close together, sideways expansion would be inhibited. The amount of free volume is further improved by causing SAP particles to break through the surfaces of both sheets thereby additionally permitting additional expansion of the particle in direction(s) perpendicular to sideways expansion when placed in contact with a liquid.

The process of the present invention may be used to cause openings or holes to be formed through either or both of the sheets by applying pressure to cause the SAP particles to break through the surface of the sheets. Should a product having such holes on only one sheet is desired, one of the sheets should be selected to be resistant to forming a hole when the pressure step is conducted. Such result may be achieved by using a sheet material that is resistant to breakage and/or is thicker than the particle and thus will not be fully penetrated upon pressing. Such "one-sided" product may be desired for use in applications leakage of absorbed liquid is undesirable, such as in a portion of a diaper core or a wipe. Of course, a "two-sided" product, i.e., one having holes formed on the surface of both sheets, is desirable for many applications when liquid absorption is desired to be maximized and when subsequent dispensing of the absorbed and collected liquid is desired.

It is advantageous to apply or place the SAP particles on the adhesive coated surface by sprinkling or otherwise arranging the particles in a manner whereby substantial touching of the applied particles is minimized. Application of the SAP particles may be performed in one or more steps. Spacing the SAP particles apart serves to maximize free volume on a sideways direction for the particles. Simply sprinkling the particles on the adhesive coated surface of the sheet is an effective application technique as no particular pattern is required although it is desirable to uniformly coat the sheet with particles. The amount of particles place on the adhesive coated surface is dependent upon the desired amount of liquid absorption.

Conventional methods useful for applying SAP particles in the above-described spaced apart manner include curtain coating, spraying, electrostatic spraying such as by Corona discharge, roll coating, and other well-known techniques.

The first and second sheets may be joined by simply placing or contacting the sheets together thereby utilizing the adhesive to cause joining. It is contemplated using sheets having an adhesive coated on the surface of both sheets and then contacting both sheets at such adhesive coated surfaces. Such embodiment serves to enhance the joining step of the process and further enhances subsequent securing of the SAP particles following the pressing and break through step. Further enhancement of the joining of the respective sheets is obtained through the application of pressure to at least one of the sheets. The steps of placing and pressing may be conducted in sequence or concurrently. Enhancing joining of the sheets and further sealing the container may be achieved by leaving a border on the sheet having the applied SAP particles and then pressing the two sheets together.

Pressure may conveniently be applied by passage of the sheets through a roll nip, rolling either or both surfaces of the joined sheets separately or at the same time, through application of pressure by a plate or the like. The process of the present invention may be practiced as a batch process or continuously. If practiced continuously it is preferred to pass webs of the respective sheets through a roll nip thereby combining the steps of joining the sheets and pressing the joined sheets. The rolls may be coated with a hard rubber surface or comprise wood, metal or any other suitable material The absorbent product of the invention may conveniently be formed by joining the edges, continuously or intermittently, of at least two sheets to form a pouch-like shape. Although openings may be created at appropriate locations on the surface following assembly of the container, it may be more convenient to create such openings prior to joining the films. Of course, if the embodiment involving forming holes by pressing a film against SAP particles is utilized, the aspect of preforming holes is not necessary, although an enhanced product could be made by using a sheet having precut or later formed holes and then forming further holes through the application of pressure against the SAP particles. Such enhancement would permit additional water contact with the sides of the SAP particles.

The absorbent product of the invention may optionally include openings at either or both of the sheet surfaces to permit liquid entry. Such openings may be sized to permit liquid entry. Typical opening configurations include, but are not limited to slits, holes of various shapes, meshes, etc.

It is contemplated that a pack or series of the absorbent product of the present invention may be used to increase the overall or total capacity to absorb liquids. Should the absorbed liquid be desired to be prevented from subsequently exiting from the pack, the outer surface of the pack can be formed from a liquid impervious material. The pack or a single element could have absorbent and shock reducing material, such as cotton fluff, absorbent woven and nonwoven fibers, etc, adjacent one or both sides of the container. Such arrangement would be suitable for diapers, wipes, feminine hygiene products and similar absorbent products.

When the absorbent product of the present invention is used as an absorbent core for products, such as a diaper, it is preferred to place the openings on only one surface of the container; i.e., the surface facing the infant. Of course the surface away from the infant would not have openings to prevent outflow of the liquid urine to undesired locations.

The product of the present invention and additional embodiments are illustrated by the sole FIGURE. The FIGURE is an illustration of a vertical cross section of the product taken along a longitudinal axis. Sheets 1 and 2 are joined together at areas 12 and 13 to form absorbent product container 3 which contains SAP particles 4, 5, and 6 which extend through sheets 1 and 2 to create openings through which liquids may enter and exit container 3. Optionally, particles 4, 5, and 6 may be non-SAP particles. In another product embodiment, instead of creating openings with the use of particles, preformed hole openings 7, 8, and 9 are utilized to permit entry and exit of liquids to container 3. As illustrated, particles 4, 5, and 6, if comprising SAP particles, are free to expand upon contact with water or another liquid such as urine, at upper, lower, and side portions thereof because of the free volume created by spacing apart particles 4, 5, and 6. Moreover, additional SAP material 10 and 11 (in the form of particles or powder, films, sheets, chips, and the like) may be optionally placed in open areas between particles 4, 5, and 6. The additional SAP material should be of a smaller size than the height of particles 4, 5, and 6 so as to cause penetration and breakage of the sheets only by particles 4, 5, and 6. The additional SAP material may be the same or different composition than the larger SAP particles. Smaller SAP particles of the same type as the larger particles would have the advantage of more rapid liquid absorption rates. Incorporating a different, second SAP material having insufficient strength to penetrate sheets 1 and 2 with stronger particles 4, 5, and 6 permits the use of weaker, more highly liquid absorbent SAP products. Thus, the use of the aforementioned starch-containing SAP material is possible despite the weakness of such very high liquid absorbency products when in combination with stronger SAP particles. In addition, the rate of liquid absorption of starch-containing SAP materials may be enhanced by using large surface area materials, such as fine powders, chips, films, etc. In such combination of SAP materials, the larger, stronger particles serve to create openings in the absorbent container through which liquids, such as water or urine, enter the area between the sheets and become absorbed and stored by the SAP material having larger absorption and storage capacity.

Combinational products of the nature described in the preceding paragraph are beneficial for use as cores for absorbent products such as diapers and wipes because equivalent liquid absorbance and storage capacity would be obtained with use of less total SAP weight than if only the stronger SAP product were used. Clearly the use of the above-described combination of SAP products would also have exhibit advantages when used in irrigation, erosion control, plant watering, root direction control, and similar applications. For such applications, the ability of the starch-containing SAP product to collect and store very high amounts of water and nutrients, on the order of at least about 1000 to about 5000 times the weight of the SAP product is very desirable. In addition, starch-containing SAP products are known to be able to easily dispense water to plant roots. In the case of the above-described combinational product, water would pass into the interior of the container via the SAP particles that extend out, desirably through the surface of the top and bottom sheets, of the container and then pass into the starch-containing SAP product where such water would be collected and stored for subsequent dispersion to plant root systems. Dispensing, like collecting, would occur through passage through the extending SAP particles. Such system would have a larger storage capacity, and hence higher efficiency, than if only particles from the extending SAP product were used.

In making the product described in the preceding paragraph, the generally described process would be followed with the second SAP product either applied as a mixture with the larger first product or applied to the first sheet separately before or after application of the first SAP product. Separate application would permit more accurate spacing of the first SAP product and is thus preferred.

Three additional product embodiments are also included in the present invention.

The first embodiment comprises a pouch-like container formed by joining two sheets together. The use of an adhesive coating on one or both sheets and pressing the sheets together is a convenient mode of joining the sheets. Prior to joining the sheets superabsorbent material, including starch-containing SAP material in the form of a powder, a foil, a sheet, and like is placed against one of the sheets and thus will become contained following joining of the sheets. One or both of the sheets contain openings created by non-superabsorbent particles such as comprising sand, metals, ceramics, wood, rock, hard, and like strong, hard plastics, and other strong, hard materials capable of penetrating through one or more of the sheets and forming an opening upon pressing the sheets.

The second product embodiment is the same as the first embodiment except that preformed openings are utilized in at least one of the sheets rather that than non-SAP particles.

The third embodiment comprises a combination of the first and second embodiments and has openings in at least one of the sheets created by the non-SAP particles and also has preformed openings.

The above described three product embodiments are especially adapted for use in long term applications such as irrigation, erosion control, plant ball watering, and in plant root system root direction control techniques. Products for such applications may be in the form of elongated strips or tubes, circular or other shaped strips or tubes, or any other shapes compatible with the intended application. For example, for irrigation applications a long strip-like container may be conveniently placed underground during ground breaking occurring when plowing and seeding. For other applications, a hole or trench may be created, the product inserted therein, and the hole then covered.

The present invention may be further understood by reference to the following Examples.

EXAMPLE 1

SAP particles having an average size of about 300 microns are applied in a spaced apart pattern to a first PVC sheet having a solid adhesive coating to cause the particles to become adhered to the sheet. A second PVC sheet is then pressed against the coated first sheet with use of a metal plate to cause the sheets to become joined together and the adhered SAP particles to penetrate and break through the surfaces of both sheets. The resultant pouch-like container product is characterized as having good liquid absorption properties when placed in contact with a liquid.

EXAMPLE 2

Example 1 is repeated except that the first sheet is made from polyethylene. The resultant product has SAP particles that are only break through the surface of the second PVC sheet. The resultant pouch-like container product is characterized as having good liquid absorption properties when placed in contact with a liquid.

EXAMPLE 3

Example 1 is repeated except that a mixture of coarse and fine SAP particles is applied to the first sheet. The coarse particles have an average particle size of about 300 microns and the fine particles have an average particle size of about 40 microns. During the pressing step only the coarse particles penetrate and break through the surface of the two sheets. The resultant pouch-like container product is characterized as having good liquid absorption properties when placed in contact with a liquid.

EXAMPLE 4

Example 1 is repeated except that a powder of starch-containing SAP is also applied to the first sheet in addition to the SAP particles having an average particle size of about 300 microns. Upon pressing the sheets together only the SAP particles having an average particle size of about 300 microns break through the surface of both sheets. The resultant pouch-like container product is characterized as having good liquid absorption properties when placed in contact with a liquid.

EXAMPLE 5

Example 4 is repeated except that non-SAP particles comprised of sand and having an average particle size of about 500 microns are substituted for the SAP particles and small openings or holes are provided through both sheets. The sheets are pressed and joined together and the sand particles break through the surfaces of both sheets. The resultant pouch-like container product is characterized as having satisfactory liquid properties when placed in contact with a liquid.

We claim:

1. A product for absorbing liquids comprising a container partially filled with particles of superabsorbent polymeric powder to create free volume in said container for said particles to expand into when in contact with a liquid, said container comprising a first film joined with a second film, said first film having an adhesive coated first side surface located on an inside surface of said container and an opposed second side surface located on an outside surface of said container and said second film having a first side surface located on an inside surface of said container and an opposed second side surface located on an outside surface of said container, said first film being sufficiently brittle for said particles of superabsorbent polymeric powder to penetrate and break through said first film, said first film having particles of superabsorbent polymeric powder of sufficiently large size to penetrate and break through said first and second side surfaces of said first film, said particles adhered to and extending through said first and second side surfaces of said first film through an opening created by penetration and breaking through said first film by said particles thereby creating further free volume for said particles to expand into when in contact with a liquid, said broken through particles spaced apart from each other to minimize touching of said broken through particles thereby enhancing liquid absorption rate and creating further free volume for said broken through particles to expand into when in contact with a liquid.

2. The product of claim 1, wherein said particles have an average particle size from about 100 microns to about 500 microns.

3. The product of claim 1, wherein said particles comprise a mixture of coarse particles having an average particle size from about 100 microns to about 500 microns and fine particles having an average particle size from about 20 microns to about 100 microns.

4. The product of claim 1, wherein said adhesive comprises a solid adhesive.

5. The product of claim 1, wherein said adhesive comprises a pressure sensitive adhesive.

6. The product of claim 1, wherein an inside surface of said second film is coated with an adhesive.

7. The product of claim 1, wherein at least one of said films contains openings at surface portions other than the openings created by said particles of superabsorbent polymeric powder.

8. The product of claim 1, wherein a superabsorbent polymeric composition is adhered to said first surface of said first film and located between said particles of said superabsorbent polymeric powder, said superabsorbent polymeric composition being of a smaller size than said particles of superabsorbent polymeric powder.

9. The product of claim 8, wherein said superabsorbent polymeric composition comprises a starch-containing composition.

10. The product of claim 7, wherein said first film further comprises an opening created by a non-superabsorbent polymeric particle that extends through said first film.

11. The product of claim 7, wherein said first film further comprises a preformed opening.

12. The product of claim 1, wherein said first film comprises plastic.

13. The product of claim 12, wherein said first film is a member selected from the group consisting of polyvinyl chloride, copolymers of polyvinyl chloride and vinyl acetate, and ethylene vinyl acetate.

14. The product of claim 1, wherein said particles extend through the surface of said first and second films.

* * * * *